United States Patent
Matich et al.

(10) Patent No.: US 11,433,550 B2
(45) Date of Patent: Sep. 6, 2022

(54) SENSOR ARRANGEMENT FOR FORCE OR TORQUE MEASUREMENT, AND A METHOD FOR THE PRODUCTION THEREOF

(71) Applicant: TECHNISCHE UNIVERSITÄT DARMSTADT, Darmstadt (DE)

(72) Inventors: Sebastian Matich, Pfungstadt (DE); Walter Albrecht, Darmstadt (DE)

(73) Assignee: WITTENSTEIN SE, Igersheim (DE)

( * ) Notice: Subject to any disclaimer, the term of this patent is extended or adjusted under 35 U.S.C. 154(b) by 544 days.

(21) Appl. No.: 16/484,227

(22) PCT Filed: Dec. 18, 2017

(86) PCT No.: PCT/EP2017/083320
§ 371 (c)(1),
(2) Date: Aug. 7, 2019

(87) PCT Pub. No.: WO2018/145800
PCT Pub. Date: Aug. 16, 2018

(65) Prior Publication Data
US 2020/0033211 A1    Jan. 30, 2020

(30) Foreign Application Priority Data

Feb. 7, 2017   (DE) .................. 10 2017 102 343.7

(51) Int. Cl.
*G01L 5/00* (2006.01)
*B25J 13/08* (2006.01)
(Continued)

(52) U.S. Cl.
CPC ............ *B25J 13/085* (2013.01); *A61B 90/06* (2016.02); *G01L 5/162* (2013.01); *G01L 5/1627* (2020.01);
(Continued)

(58) Field of Classification Search
CPC .......... B25J 13/085; B25J 9/003; B25J 19/02; A61B 90/06; A61B 34/35; A61B 2090/066; G01L 5/1627; G01L 5/162
See application file for complete search history.

(56) References Cited

U.S. PATENT DOCUMENTS 3,295,224 A   1/1967  Cappel
4,628,745 A * 12/1986 Hatamura ............. G01L 1/2218
                                                         73/862.042

(Continued)

FOREIGN PATENT DOCUMENTS

CN   104858892 A   8/2015
DE     4101732 A1  7/1992
(Continued)

OTHER PUBLICATIONS

Multi-Axis Force/Torque Sensor Based on Simply-Supported Beam and Optoelectronics. Nov. 17, 2016, vol. 16 (11), p. 1936 https://library.uspto.gov/discovery/fulldisplay?docid=cdi_doaj_primary_oai_doaj_org_article_7b6c521e4e1b4228b56f0ff4b14acf03&context=PC&vid=01USPTO_INST:01USPTO&lang=en&search_scope=MyInst_an.*

(Continued)

*Primary Examiner* — Max H Noori
*Assistant Examiner* — Masoud H Norri
(74) *Attorney, Agent, or Firm* — Patent Portfolio Builders PLLC

(57) ABSTRACT

A sensor arrangement for measuring at least one component of a force or a torque includes a sensor assembly having a first contact structure and a second contact structure, between which the at least one component of the force or torque is to be measured, and a plurality of sensor elements. The plurality of sensor elements are each connected by way of a first joint to the first contact structure and by way of a second joint to the second contact structure and configured (Continued)

to measure the component of force or torque between the first contact structure and the second contact structure. The first contact structure, the second contact structure and the plurality of sensor elements form a rolled-up structure that extends like a jacket along a surface of the sensor arrangement.

14 Claims, 10 Drawing Sheets

(51) Int. Cl.
| | |
|---|---|
| *A61B 90/00* | (2016.01) |
| *G01L 5/162* | (2020.01) |
| *G01L 5/1627* | (2020.01) |
| *A61B 34/35* | (2016.01) |
| *B25J 9/00* | (2006.01) |
| *B25J 19/02* | (2006.01) |

(52) U.S. Cl.
CPC ......... *A61B 34/35* (2016.02); *A61B 2090/066* (2016.02); *B25J 9/003* (2013.01); *B25J 19/028* (2013.01)

(56) References Cited

U.S. PATENT DOCUMENTS

| | | | |
|---|---|---|---|
| 4,695,963 A * | 9/1987 | Sagisawa | G01L 5/228 414/730 |
| 5,063,788 A | 11/1991 | Ch'Hayder et al. | |
| 10,620,067 B2 | 4/2020 | Doll | |
| 2006/0169060 A1 * | 8/2006 | Okada | G01L 5/165 73/862.043 |
| 2009/0038413 A1 | 2/2009 | Seibold et al. | |
| 2009/0301217 A1 * | 12/2009 | Kurtz | G01L 5/223 73/847 |
| 2011/0314935 A1 | 12/2011 | Krippner et al. | |
| 2012/0266648 A1 * | 10/2012 | Berme | A61B 5/1112 73/862.041 |
| 2020/0293112 A1 * | 9/2020 | Richter | G06F 3/011 |
| 2022/0040866 A1 * | 2/2022 | Nitz | G05B 19/423 |

FOREIGN PATENT DOCUMENTS

| | | |
|---|---|---|
| DE | 10013059 A1 | 9/2001 |
| DE | 102007017862 A1 | 10/2008 |
| DE | 102007037262 B3 | 12/2008 |
| DE | 102015003919 A1 | 10/2015 |
| DE | 102015215099 B3 | 12/2016 |
| EP | 2260279 A2 | 12/2010 |
| KR | 20120069851 A | 6/2012 |
| WO | 2009106407 A2 | 9/2009 |

OTHER PUBLICATIONS

Office Action created on Sep. 30, 2020 in related/corresponding DE Application No. 10 2017 102 343.7.
International Search Report dated Mar. 27, 2018 in related/corresponding International Application No. PCT/EP2017/083320.
Written Opinion dated Mar. 27, 2018 in related/corresponding International Application No. PCT/EP2017/083320.

* cited by examiner

SENSOR ARRANGEMENT FOR FORCE OR TORQUE MEASUREMENT, AND A METHOD FOR THE PRODUCTION THEREOF

The present invention relates to a sensor arrangement for measuring at least one component of a force or a torque and a method for producing the same, and more particularly to a miniaturized force-torque sensor with a hexapod structure made in rolling technology.

BACKGROUND

Force or torque sensors—especially in miniaturized form—can be used, for example, in telemanipulators for minimally invasive surgery. Such telemanipulators consist, for example, of a console by means of which the surgeon can control two manipulation arms located inside the body. At the ends of the manipulators there are tools (end effectors), such as grippers or scissors, that interact with the tissue.

A disadvantage of such telemanipulators is the loss of haptic perception. In order to be able to reproduce for the surgeon the forces acting in the body, the contact forces between the manipulation arms and the tissue are measured. In order to keep a resulting measurement error as small as possible and to improve the signal quality, the force-torque sensors used for this purpose should be integrated in the manipulation arm as close as possible to the end effector. However, due to the narrow spatial relationships in the body, especially small sensors are required. For example, sensors that are less than 10 mm in diameter and no longer than 15 mm in diameter are desirable. In addition, it is desirable for such sensors to be inexpensive to manufacture in large quantities using simple means.

For example, known sensors that can measure forces in three spatial directions as well as torques about the three spatial directions are based on a deformation body with a hexapod structure, also known as a Stewart-Gough platform. The deformation body deforms when a force is applied and these deformations can be detected by strain gauges. Such a hexapod structure is disclosed, for example, in U.S. Pat. No. 3,295,224 A, in DE 10 2007 017 862 A1, in US 2011/0314935 A1 or in EP 2,260,279 A2. A disadvantage of these known sensors is that they comprise a three-dimensional deformation body that is complicated to produce, with strain gauges attached thereto. Due to their monolithic design, the positioning, alignment or sticking and pressing of the strain gauges must be done in manual steps requiring a lot of effort. In particular, the positioning of the strain gauges is very difficult due to the selected geometry and the desired small size, so that this process can hardly be automated, if at all.

Therefore, there is a need for alternative sensor arrangements and concepts that can be used for said applications and overcome at least some of the above-mentioned problems.

SUMMARY

Exemplary embodiments of the present invention relate to a sensor arrangement for measuring at least one component of a force or a torque. The sensor arrangement comprises the following features: a first contact structure and a second contact structure, between which the at least one component of the force or the torque is to be measured. The sensor arrangement further comprises a plurality of sensor elements that are connected to the first contact structure by way of a first joint and to the second contact structure by way of a second joint, respectively, and which are configured to measure the component of the force or the torque between the first contact structure and the second contact structure. The first contact structure, the second contact structure, and the plurality of sensor elements form a rolled-up sensor structure which extends along a surface of the sensor arrangement in the form of a jacket or spiral.

The terms "contact structure" or "sensor structure" or other structures are to be construed broadly and do not necessarily refer to a composite of parts. Rather, the structure should be left open and in particular also comprise one-piece parts or elements. A contact structure should also be understood to mean whatever is designed for contacting (mechanically or electrically). For example, the defined contact structures can be designed to provide means for a force input or a force output. The term "jacket-shaped" in connection with the sensor structure is to be understood that the sensor structure is not monolithic, but was joined together along a seam.

By way of example, the plurality of sensor elements can comprise six sensor elements defining a hexagonal structure and which are inclined relative to the first contact structure and the second contact structure such that three different force components and/or three different torque components can be independently measured. The hexagonal structure can in particular be a hexapod structure. Optionally, the plurality of sensor elements are disposed as a tripod, screw, or honeycomb structure.

Optionally, the plurality of sensor elements can each comprise a bridge structure having a thinned portion and at least one strain gauge on the thinned portion to measure a strain of the thinned portion as a result of the application of the force or torque. A strain gauge can mean strain gauge strips, but can also comprise one or more piezo elements and can be disposed on an inner region after rolling up. The piezo elements can comprise one or more metal films, but they can also be designed as silicon measuring elements (piezoresistive measuring effect). Optionally, additional piezo elements (actuators) can be disposed laterally next to existing strain gauges. For example, the actuators can be used to induce high-frequency oscillations in the structure, which can minimize the hysteresis effect. This would have the advantage that even with low material quality, very accurate measurements are possible. Optionally, the strain gauges can also measure compressions (i.e., negative strains).

The bridge structure may, for example, have a U-shaped cross-sectional profile with two opposing sections between which a recess is formed and which are bridged by a connecting section as a thinned section. Optionally, the first contact structure and the second contact structure can couple at the two opposing sections, and the strain gauge can be formed on the connecting section. This makes it possible to exert a lever force on the connecting section during the measurement of the force component or the torque and thus to achieve an increase in strain.

Optionally, the first joint and/or the second joint can each be a flexure joint, wherein the flexure joint has a reduced, in particular square, cross-sectional area. The square cross-section is not absolutely necessary (but it can be easily produced by cutting or milling). Considering excess strain at the edges, a round cross-sectional area would be simpler. For example, this cross-sectional area can be defined perpendicular to a connecting line between the first and second contact structure. The particular choice of a cross-sectional narrowing represents a compromise between a reliable coupling of the opposite sections (and thus a sufficient grip) and ease of deformability, for example.

Optionally, the sensor assembly further comprises a first lid and/or a second lid, wherein the first lid is attached to the first contact structure and the second lid is attached to the second contact structure. The lids can in particular comprise means for force input and force output. These means include, for example, retaining elements or threads to produce a screw connection.

The sensor arrangement can be used, for example, for power transmission to a tool. For this purpose, the first lid and the second lid can define an axial axis about which the jacket-shaped sensor structure is disposed. In addition, the first lid and the second lid can each have an opening through which the axial axis passes. The axial axis can also be defined by a corresponding arrangement of the means for force input and force output. The rolled-up sensor structure can also define an interior space for routing through the sensor assembly optical and/or electrical lines and/or elements for operating the tool along the axial axis. Integrated circuits for evaluating the measuring elements can also be present in the sensor structure so as to reduce the number of cables. Optionally, the first contact structure and the second contact structure each comprise a plurality of segments. In addition, in each case a sensor element can be formed between two corresponding segments. A plurality of sensor sections is formed in this way. Optionally, the segments each include a pin extending away from the sensor module. The first lid and the second lid can each have a plurality of grooves that are disposed such that the pins of the first and second contact structure are insertable into the grooves. Optionally, the pins can be firmly connected to the lids by gluing and/or soldering and/or welding (e.g., resistance welding). Other techniques include joining by forming, wherein crimping, riveting or bending can be sensibly implemented, for example. This would have the advantage that only a small heat input takes place, if at all. The lid also fulfills the function of connecting the contact structures.

Optionally, the sensor arrangement comprises additional sensor elements on the segments of the first contact structure and/or on the segments of the second contact structure. For example, in each case one sensor element can be connected to one of the additional sensor elements to form a half-bridge circuit. Through the use of other additional sensor elements, a full bridge circuit of sensor elements can likewise be achieved. For example, the additional sensor elements are fixed to the segments in such a way that they allow a comparison measurement in order to increase accuracy. For example, they can be applied to a non-strained portion and/or can be sensitive in another direction.

Embodiments of the present invention also relate to use of the previously described sensor assembly as a miniaturized force-torque sensor for minimally-invasive surgery.

The present invention also relates to a method of manufacturing a sensor for measuring at least a force and a torque. The method comprises the following steps:

Providing a planar sensor structure having a first contact structure and a second contact structure with a plurality of sensor elements connected in a jointed manner therebetween; and Rolling up the planar sensor structure, so that the first contact structure and the second contact structure and the plurality of sensor elements extend in a jacket or spiral shape around an axial axis.

Optionally, providing the planar sensor structure can include the steps of:

Providing a flexible body;

Structuring the flexible body to form the first contact structure and the second contact structure interconnected by bridge members; and Forming at least one respective strain gauge on the bridge elements.

For example, the structuring can include at least one of the following operations: milling, cutting, grinding, laser machining (such as laser sintering or laser cutting), etching, cutting (punching), embossing, 3D printing.

The manufacturing can be carried out by a two-stage process suitable for a favorable mass production, comprising the following steps:

1. A sheet metal is machined on the mill, with structures rising in the plane being milled.
2. The pre-processed plate comes to the laser and the structures are cut out.

Tolerance-critical structures can be worked out precisely on the milling machine. In addition, the milling time can be massively shortened if the structure is cut out and not milled out. In addition, stress-relief annealing of the planar sensor structure can be done to eliminate existing stresses in the material. Thus, a significant improvement in the measurement can be achieved by strain gauges.

Optionally, the rolling up step comprises:

inserting the planar sensor structure into a rolling device comprising a guide and an angled section, the guide being configured to receive the planar sensor structure, and moving the planar sensor structure toward the angled section, whereby the planar sensor structure is bent in sections and the jacket-shaped structure is generated.

The method can optionally include placing a first lid and a second lid on opposite sides of the rolled-up sensor structure. In addition, the rolled-up sensor structure can be inserted in a cylindrical or prism-shaped mounting aid. Finally, by exerting a pressure on the opposite lid, the jacket-shaped sensor structure can be aligned axially-symmetrically.

Embodiments of the present invention provide the following advantages in particular:

First, the sensor assembly according to the present invention can be easily produced in miniaturized form. The problems of the known sensors with respect to the manufacture of the deformation body and the subsequent application (e.g., gluing) of strain gauges on the deformation body and the contacting and wiring of the applied strain gauges are overcome by exemplary embodiments in that the sensor array is made planar and that the spatial shape of the deformation body is achieved by a rolling-up process.

In contrast to the conventional arrangements in which the inner sides of the cylinder cannot be reached due to their monolithic design and thus the application of the strain gauges on the inside is difficult or impossible, this is not a problem in embodiments—even with a high degree of miniaturization.

Strain gauges can be simple film strain gauges or silicon strain gauges or a film with a plurality of measuring elements applied in one work step. As a result, a cost-effective production is possible. In the exemplary embodiments, the forces can be measured in all three spatial directions x, y and z and the torques about these axes can be measured independently of one another. Due to the planar manufacturing, it is also possible to use thin-film and thick-film techniques for the production of the sensors. These techniques, which are suitable for large-scale use, do not work for the aforementioned monolithic structures. Embodiments also make it possible to imprint strain gauges or to structure them by means of paste and lasers.

BRIEF DESCRIPTION OF THE FIGURES

The exemplary embodiments of the present invention will be better understood from the following detailed description and the accompanying drawings, which should not be construed as limiting the disclosure to the specific embodiments but are for explanation and understanding only.

DETAILED DESCRIPTION

Figure 1:
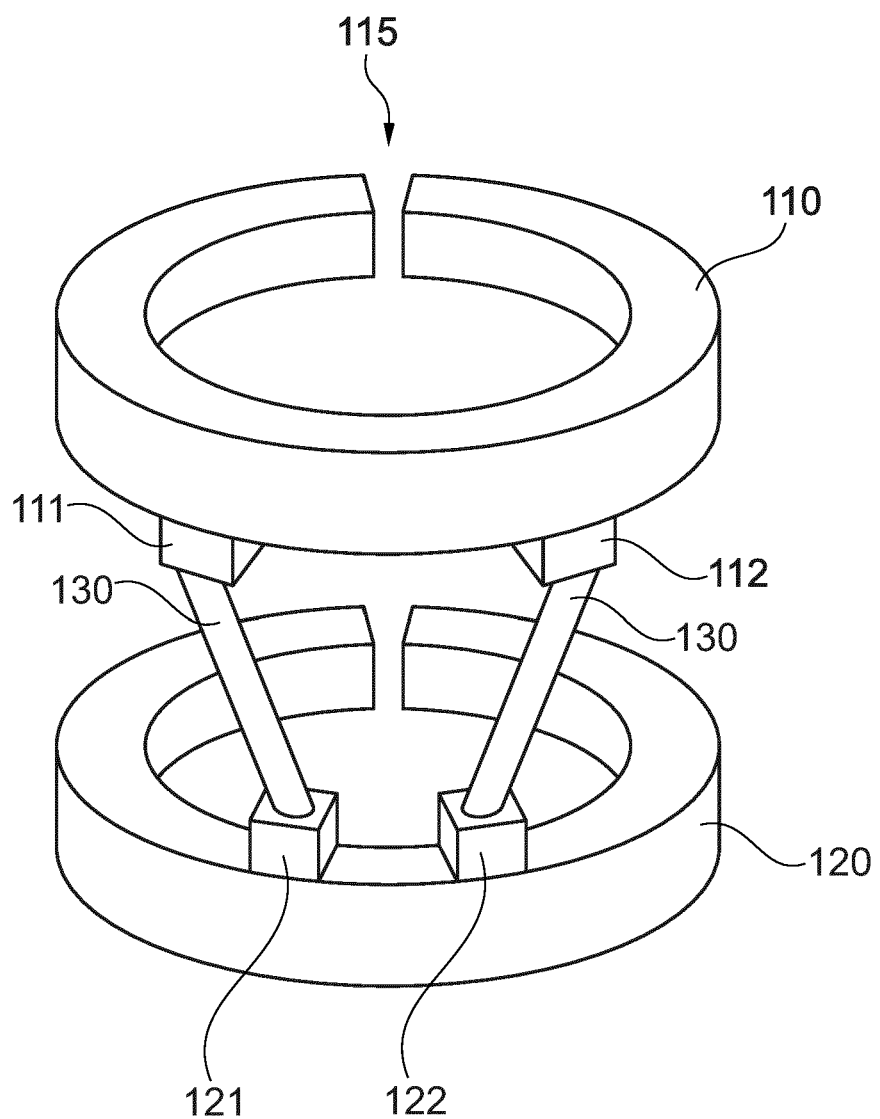
FIG. 1 shows a sensor arrangement for measuring at least one component of a force or a torque according to an embodiment of the present invention.

FIG. 1 shows a sensor arrangement for measuring at least one component of a force or a torque according to an embodiment of the present invention. The sensor arrangement comprises a first contact structure 110 and a second contact structure 120, between which at least one component of the force or the torque acts. In addition, the sensor arrangement comprises a plurality of sensor elements 130 connected to the first contact structure 110 by way of a first respective joint 111, 112 and to the second contact structure 120 by way of a respective second joint 121, 122. The sensor elements 130 are configured to measure the component of the force or torque between the first contact structure 110 and the second contact structure 120. This can be done by measuring strains, for example (e.g., using strain gauges). However, it is also conceivable to use piezo elements or other measuring sensors or sensor principles (such as optical methods) suitable for force measurement. As already stated, the piezo elements can comprise one or more metal films or be designed as silicon measuring elements (piezoresistive measuring effect). As an option, additional piezo elements (actuators) can be disposed next to the existing strain gauges. For example, the actuators can be used to induce high-frequency oscillations in the structure, which can minimize the hysteresis effect. This would have the advantage that even with low material quality, very accurate measurements are possible.

According to the present invention, the first contact structure 110, the second contact structure 120, and the plurality of sensor elements 130 form a rolled-up structure that extends in a jacket-like manner along a surface of the sensor arrangement. The jacket-like rolled-up structure with the first contact structure 110 and the second contact structure touch each other along a connection point 115. Optionally, there can also be a gap formed there, which can be closed with an adhesive, a solder seam or otherwise. The gap 115 is then recognizable, for example by the different material used for closing.

In the exemplary embodiment of FIG. 1, by way of example only two sensor elements 130 are shown. Advantageously, at least three sensor elements are formed. On the one hand, this provides sufficient stability in holding the first and second contact structures 110, 120, but also allows three independent measurements for three of the six components (three translational forces and three torque forces). However, the present invention should not be limited to a particular number of sensor elements 130—depending on the application more or less sensors can be present.

Figure 2:
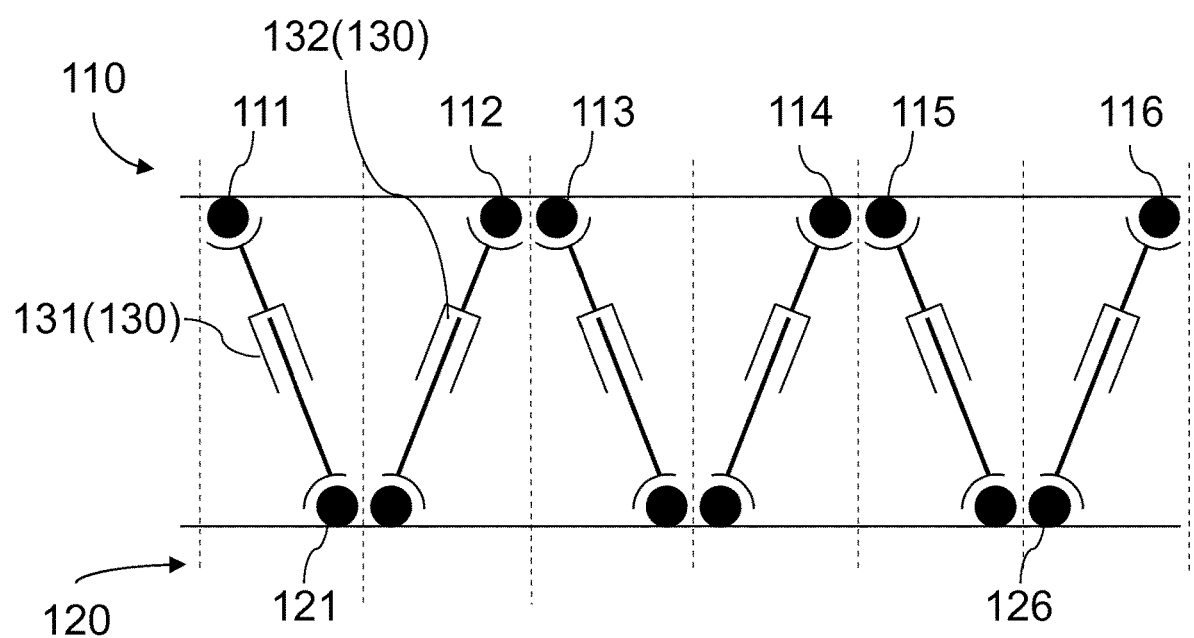
FIG. 2 schematically shows a sensor structure according to an embodiment in the unrolled shape.

FIG. 2 shows the sensor arrangement in the unrolled form with a total of six sensor elements 131, 132, . . . 136. The six sensor elements 131 . . . 136, shown by way of example, are connected, by way of joints 111, 112, . . . 121, 122, . . . , to the first contact structure 110 and the second contact structure 120, respectively. Thus, the first sensor element 131 is connected to the first contact structure 110 using a first joint 111 and to the second contact structure 120 using a second joint 121. In the same way, the second sensor element 132 is in turn connected by way of a corresponding first joint 112 to the first contact structure 110 and by way of a corresponding second joint 122 to the second contact structure 120. Similarly, all other sensor elements are connected on both sides by way of joints to the first contact structure 110 and the second contact structure 120.

For example, the first joints 111, 112, . . . 116 and the second joints 121, 122, . . . , 126 can be flexure joints that allow a relative tilting of the sensor elements 131, . . . 136 relative to the first contact structure 110 and the second contact structure 120, respectively. The sensor elements 131, . . . 136 can also be inclined relative to the first contact structure 110 and the second contact structure 120. Although this is not absolutely necessary, it has the advantage that the sensitivity and the stability of the sensor arrangement is improved. In particular, it has been found that a very high sensitivity can be achieved at an angle of inclination a of between 30° and 60° (or at about 35° or at about 55° or between these values) relative to a vertical axis (vertical connecting axis between the first and second contact structure 110, 120).

Figure 3:
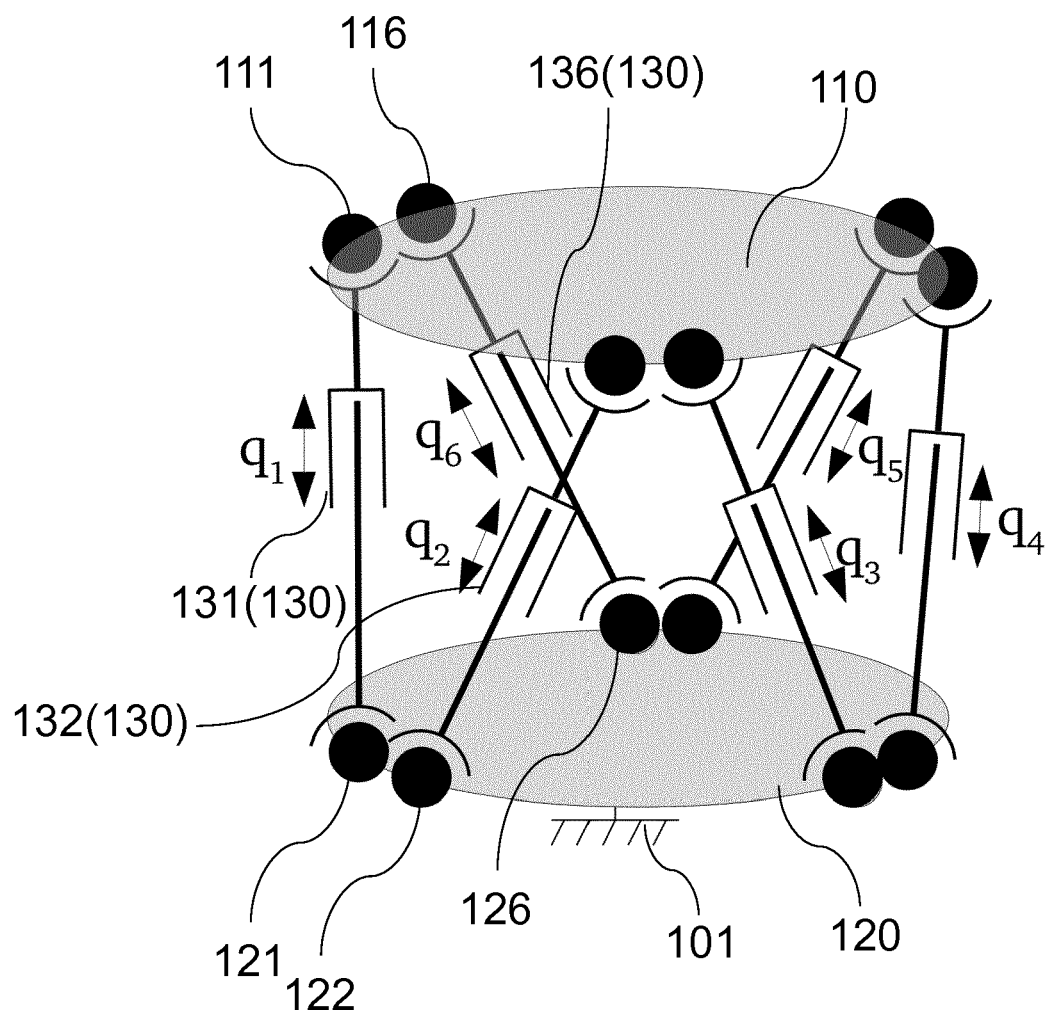
FIG. 3 schematically shows the rolled-up sensor structure of FIG. 2.

FIG. 3 schematically shows the rolled-up sensor structure after the planar sensor structure from FIG. 2 has been rolled-up into a cylindrical or prism shape. In the exemplary embodiment shown, in turn, the first contact structure 110 is disposed at the top and the second contact structure 120 is disposed at the bottom. Tilting or movement of the first contact structure 110 relative to the second contact structure 120 causes at least some of the sensor elements 131, . . . 136 to change their length. This change in length is represented by the variables q1, q2, . . . q6 for the individual sensor elements 131, 132, . . . 136. Moreover, the tilting or movement of the first contact structure 110 relative to the second contact structure 120 causes the sensor elements 130 to tilt relative to the first contact structure 110 and the second contact structure 120, the tilting being the purpose for which the articulated connections 111, . . . 116 and 121, . . . 126 are designed.

The illustration shown in FIG. 3 is a simplified representation in which the strip-shaped sensor elements 131, . . . 136 disposed along the circumference of the sensor structure, which is rolled up in a cylindrical or prismatic manner, are ideally not flexible with respect to one another and can only change in length to produce a corresponding electrical signal. To this end, for example, the second sensor arrangement 120 can be connected to ground 101 and corresponding signals can be detected and output by way of the first contact structure 110. The second contact structure 120 represents a base and the first contact structure 110 represents a platform. The six signals detected, which represent a relative change in length of the individual strip-shaped sensor elements 130, can be evaluated and used to determine the three possible lateral force directions and the three possible torque directions.

FIG. 3 thus shows a kinematic structure of a hexapod (Stewart-Gough platform), the unrolling and segmentation of which leads to the illustration from FIG. 2.

Figure 4:
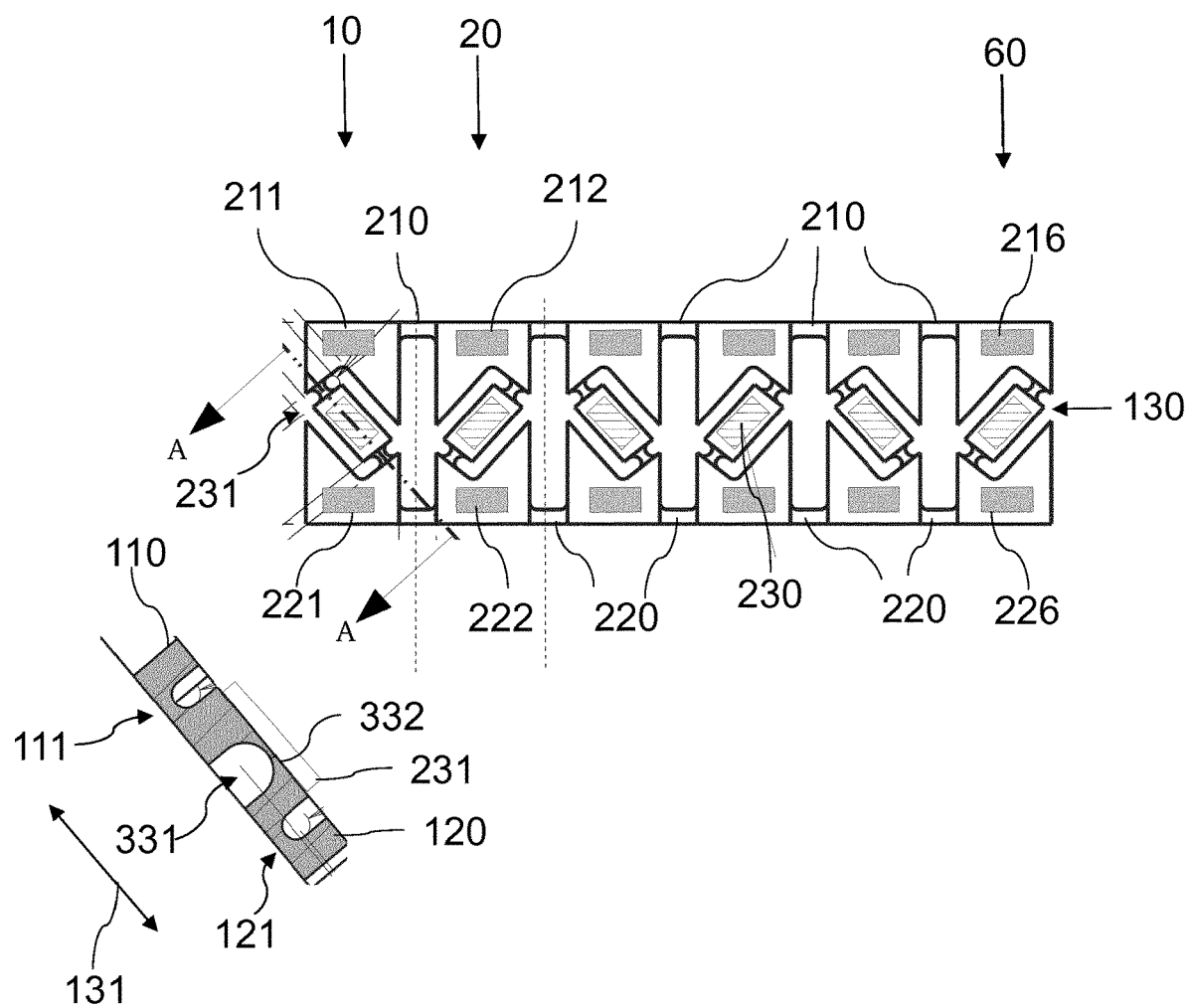
FIG. 4 shows a detailed view of the unrolled sensor structure according to further embodiments.

FIG. 4 shows a detailed view of the unrolled sensor structure, wherein the first contact structure 110 and the second contact structure 120 are disposed in a plane in common with the sensor elements 130. In the embodiment of FIG. 4, a total of six sensor sections 10, 20, . . . 60 are formed (the separation occurs as shown by the dashed lines), each section comprising a segment of the first contact structure 110 and a segment of the second contact structure 120 and a sensor element 130. The six sensor sections 10, 20, . . . 60 are connected to one another by way of first connecting sections 210 and second connecting sections 220. By way of example, each sensor element 130 comprises a strain gauge 230.

The first connecting sections 210 in each case connect the corresponding segments of the first contact structure 110. The second connecting sections 220 in each case connect the corresponding segments of the second contact structure 120. For example, the first connecting sections 210 and the second connecting sections 220 are thinned sections so that it becomes possible to roll up the illustrated planar sensor structure into a cylinder or prismatic shape such that the first section 10 connects to the sixth sensor section 60 or at least is in the vicinity thereof. For example, the connecting sections 210, 220 can be film joints.

In addition, each sensor section 10, 20, . . . 60 includes a contact pad 211 on the first contact structure 110 and a contact pad 221, 222, . . . 226 on the second contact structure 120. The contact pads 211, 212, . . . 216 and 221, 222, . . . 226 are designed to establish electrical contact between the respective contact pad and the strain gauge 230, as an example. The contact pads 211, 221, 212, 222 also provide space for primary electronics or for contacting (e.g., by bonding) to enable signal acquisition for an (external) evaluation unit. The joints 111, 121 for holding the sensor elements 130 can in turn be flexure joints or ball joints.

The lower left of FIG. 4 shows a cross-sectional view along the cross-sectional line A-A passing through the first sensor element 131 that is fastened to the first contact structure 110 by way of the first flexure joint 111 and to the second contact structure 120 by way of the second flexure joint 121. The cross-sectional view shows that the first flexure joint 111 and the second flexure joint 121 are formed by thinned sections, so that relative bending is possible between the first contact structure 110 and the first sensor element 131 and between the second contact structure 120 and the first sensor element 131 at these sections.

In addition, the first sensor element 131 is bridge-shaped by forming a recess 331 (or cavity or cutout) in a central region, the recess being bridged by a thinned section 332 as a connecting section on whose surface the strain gauge 231 is formed as an example.

The recess 331 is located on a same side of the bridge-shaped structure as the thinned portions forming the first flexure joint 111 and the second flexure joint 121. This design offers the following advantage. A force acting along the section line A-A is introduced, by way of the flexure joints 111, 121, to the side where the recess 331 is present and therefore is not directly forwarded on. Because of the recess 331, the force is diverted and bends the connecting section 332. The bridge structure moves apart like an accordion. This bending is detectable by the exemplary strain gauge 231 as an elongation (or compression).

It is particularly advantageous if the depth of the recess 331 and the position of the first flexure joint 111 and/or the second flexure joint 221 are selected so that the component of the force or the torque exerts a lever force on the connecting section 332 and thus leads to an increased strain (or excess strain). The level of increase can be flexibly adjusted, for example by the depth of the recess 331 or the thickness of the connecting section 332 at the thinnest point.

All other sections and sensor elements 130 can be designed in the same shape. The individual sensor elements 130 in the sensor sections 20, . . . 60 differ only in that the relative orientation to the first contact structure 110 and to the second contact structure 120 is changed so that they are particularly sensitive to other spatial directions or directions of rotation. For example, adjacent bridge structures of the sensor elements 130 can each extend at a right angle (or between 60° . . . 120°) relative to each other so that they are particularly sensitive to orthogonal forces acting on one another.

The applied strain gauges 231 can be film strain gauges or silicon strain gauges connected as a quarter bridge, for example. It is also possible to use a plurality of measuring strips, which are interconnected as a half or full bridge (see also FIG. 7).

Figure 5:
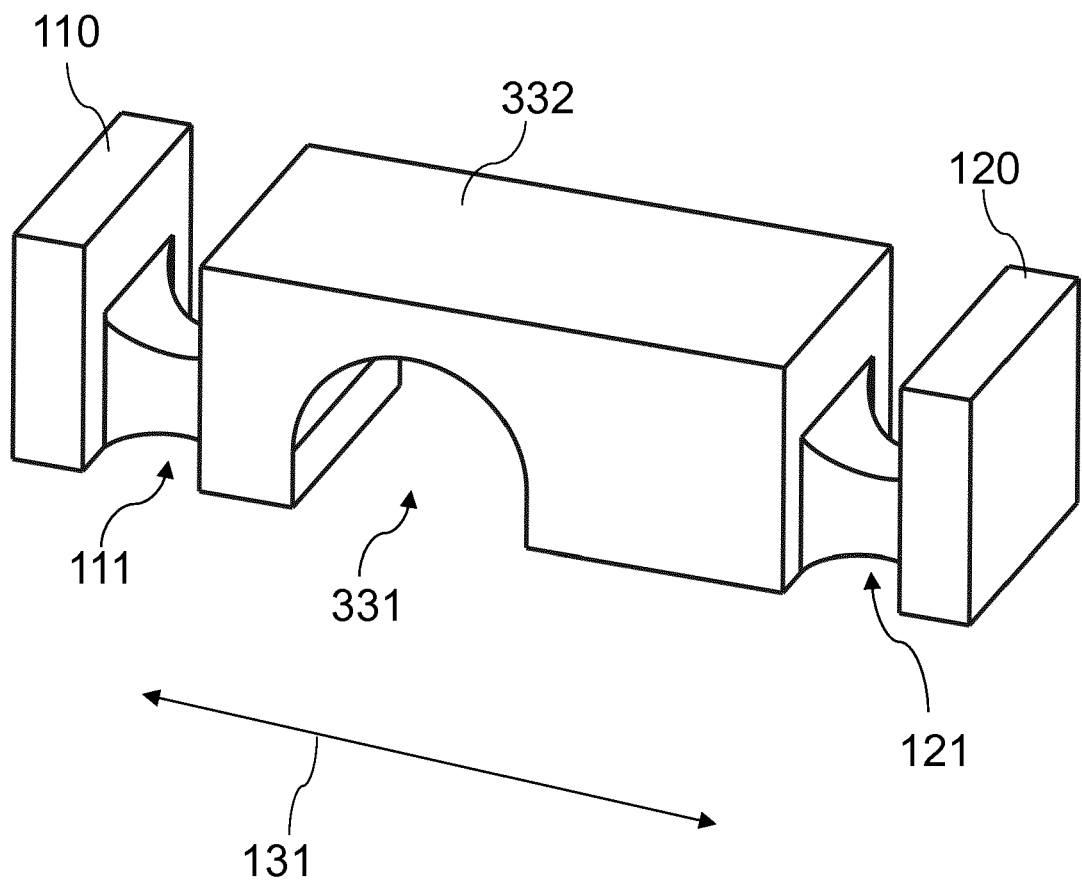
FIG. 5 shows an enlarged view of the bridge-shaped structure shown in FIG. 4 below.

FIG. 5 shows an enlarged view of the bridge-shaped structure for the first sensor element 131 shown in FIG. 4 at the bottom left, the structure being shown between parts of the first contact structure 110 and the second contact structure 120 firmly connected by means of the first flexure joint 111 and the second flexure joint 121. The geometry of the flexure joints 111, 121 is selected such that the first contact structure 110 can tilt relative to the first sensor element 131 without causing a fracture of the first flexure joint 111. Similarly, the second flexure joint 121 is configured to allow relative bending or tilting of the second contact structure 120 relative to the first sensor element 131. This can be achieved by a suitable choice of material (e.g., with a suitable ductility).

In particular, however, the cross-sectional area perpendicular to the extension of the bridge can be significantly smaller than that of the bridge structure on both sides of the recess 331 (e.g., less than 50% or less than 30%). This can, for example, be done by way of notches, which can be made by milling, for example. It is particularly advantageous if this cross-sectional area is reduced in both spatial directions (e.g., in the form of a square) in order to achieve a joint effect in both directions.

Figure 6:
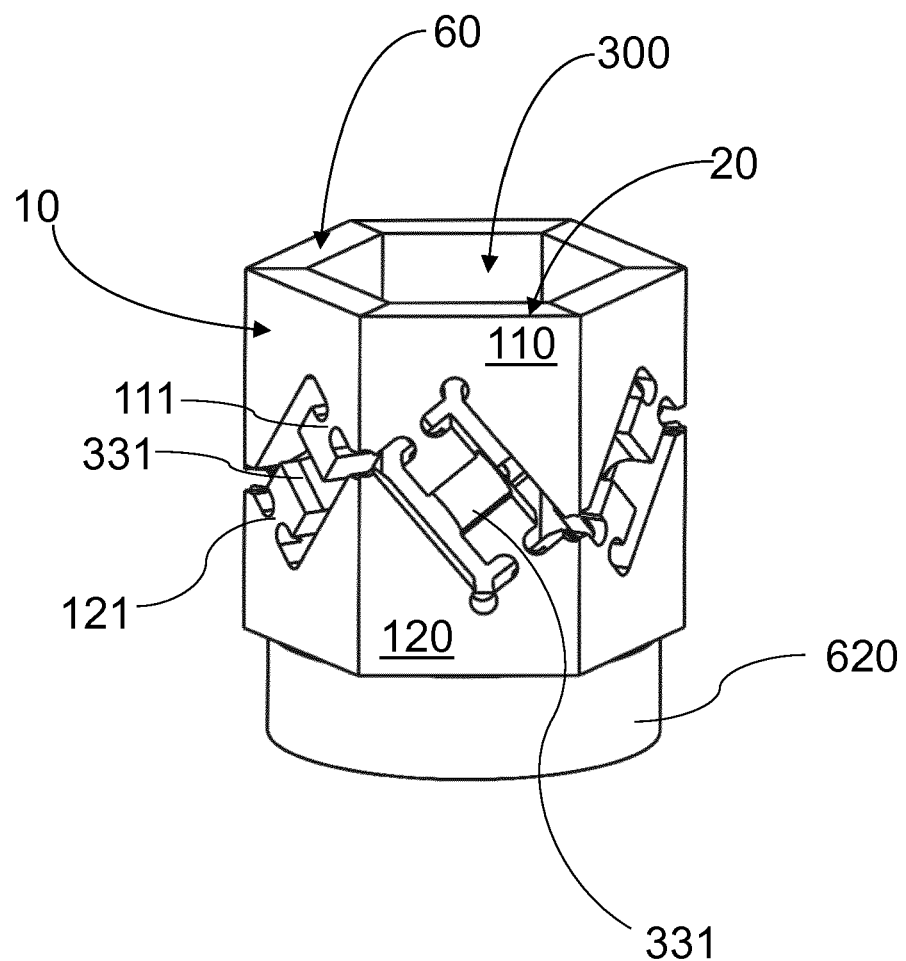
FIG. 6 shows the planar sensor structure shown in FIG. 4 in the rolled-up state.

FIG. 6 shows the planar sensor structure shown in FIG. 4 in the rolled-up prism-shaped state, so that an inner space 300 is formed. The rolling up can take place in such a way that the bridged recesses 331, 332, . . . of the bridge structures are located on an outer surface (facing away from the inner space 300) of the prism-shaped rolled-up sensor arrangement. It is thereby achieved that the exemplary strain gauges 230 are disposed in the inner space 300 and protected. In addition, the flexure joints 111, 121, . . . can terminate flush with the first contact structure 110 and flush with the second contact structure 120 on the outer surface shown. The corresponding notches between the first contact structure 110 and the sensor element 131 and between the second contact structure 120 and the sensor element 131 are located in the inner region 300 (see also FIG. 5).

As in the illustrations shown above, six sensor sections 10, 20, . . . 60 are connected to one another in the rolled-up structure, resulting in a hexagonal prism having a hexagonal base and cross-sectional plane.

FIG. 6 also shows, by way of example, a lid 620 that holds the second contact structure 120 and can be glued or welded, for example. On the upper side along the first contact structure 110, a lid can also be formed, which is not shown in FIG. 6. The lids on the top and bottom are used for force input and force output to trigger the control elements (e.g., for tools or end effectors that can be present at the ends of the manipulators).

Figure 7A:
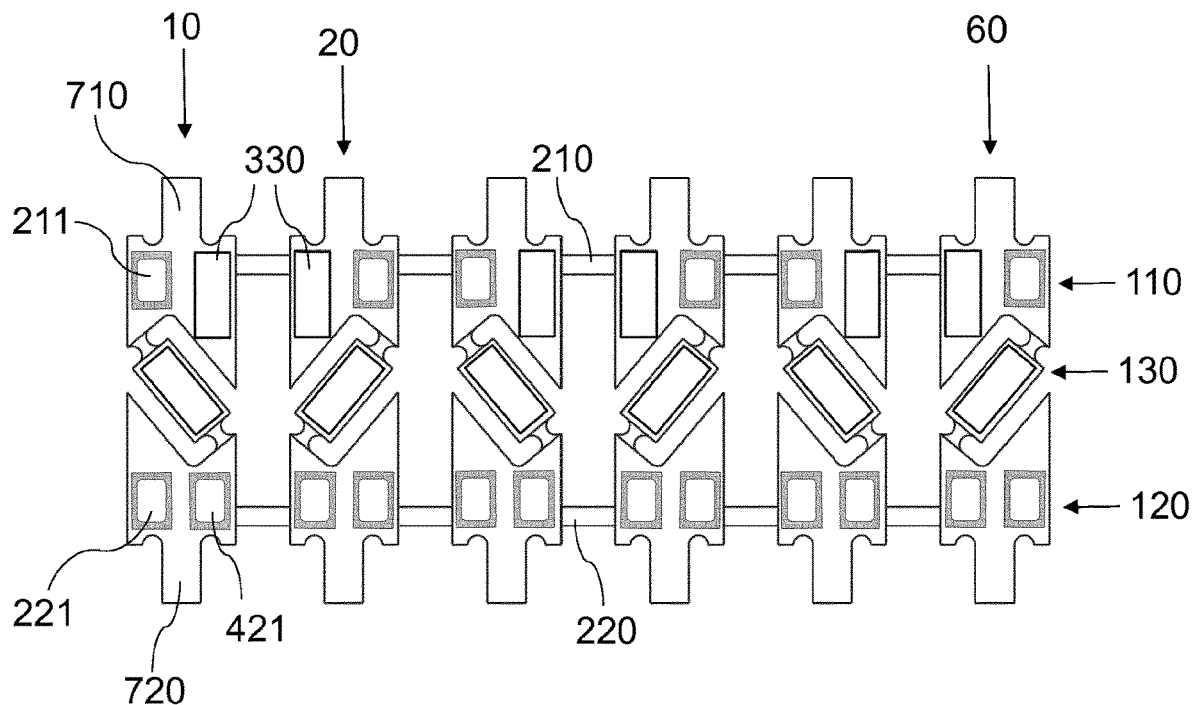
FIGS. 7A, 7B show a planar sensor structure according to another embodiment of the present invention.

FIG. 7A shows a further embodiment of the present invention that differs from the exemplary embodiment shown in FIG. 4 in that each sensor section 10, 20, . . . 60 has three contact pads 211, 221, 421, and in addition to the already existing sensor element 130 has at least an additional sensor element 330. The at least one additional sensor element 330 can be formed in a region of the contact structures 110, 120 that deforms very slightly if at all during the force or torque measurement, so that it can be used for a comparison measurement. For example, by means of the at least one additional sensor element 330, a half-bridge structure can be generated that is contacted in each case by way of the three contact pads 211, 221, 421. The three contact pads 211, 221, 421 are correspondingly electrically connected to the respective sensor elements 130 and additional sensor elements 330. For example, a contact pad 211 and an additional sensor element 330 are formed on the segments of the first contact structure 110 in each section 10, 20, . . . and two contact pads 221, 421 are formed on each of the segments of the second contact structure 120. However, the distribution can also be chosen differently.

In addition, each segment of the first contact structure 110 and each segment of the second contact structure 120 in the embodiment shown comprises a peg-shaped section. Thus, the first section 10 comprises a first pin 710 on the first contact structure 110 and a second pin 720 on the second contact structure 120. The other sections 20, . . . , 60 can be formed in the same way.

Figure 7B:
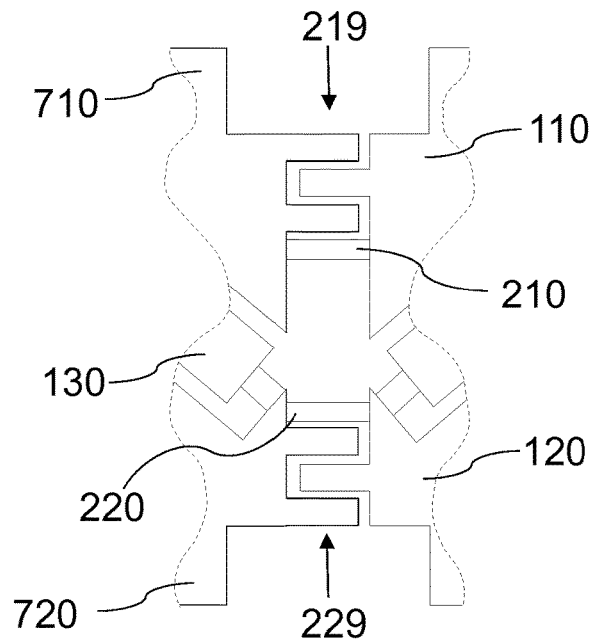

FIG. 7B shows another embodiment of the present invention that differs from the embodiment of FIG. 7A in that the first and second connecting sections 210, 220 are disposed closer to the sensor elements 130. In addition, a first comb structure 219 is additionally formed between the segments of the first contact structure 110 and a second comb structure 229 is formed between the segments of the second contact structure 120. The comb structures 219, 229 are defined by meshed combs that increase the adhesion surface between the first contact structure 110 and the second contact structure 120.

For example, prior to rolling up the planar sensor structure, the first contact structure 110 and the second contact structure 120 are not connected together along the first and second comb structures 219, 229 (but only by way of the first and second connection elements 210, 220). After rolling up, the first and second comb structures 219, 229 can be used to connect the first and second contact structures 110, 120 together (e.g., by way of gluing, melting, soldering, laser treatment, etc.). The increased adhesion surface thus creates a reliable connection. This offers the advantage that the lids are not necessarily required (see FIGS. 8A and 8B). The pins 710, 720 are also optional in this embodiment. However, they can be used to achieve a coupling of the sensor arrangement to other elements.

The sensor elements 130 are formed in the same manner as described above, so that repeated description is not required.

Figure 8A:
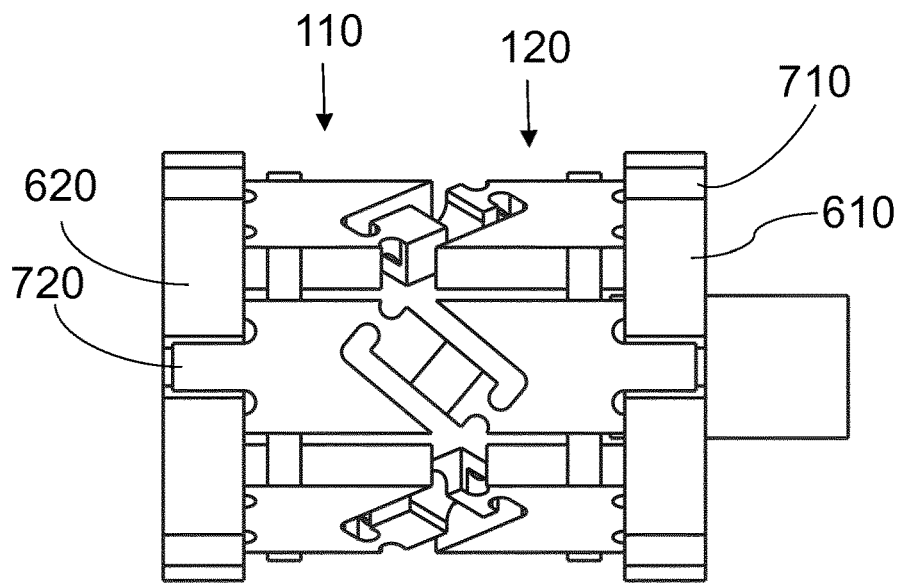
FIGS. 8A, 8B show a side view and a spatial view of the rolled-up sensor structure.
Figure 8B:
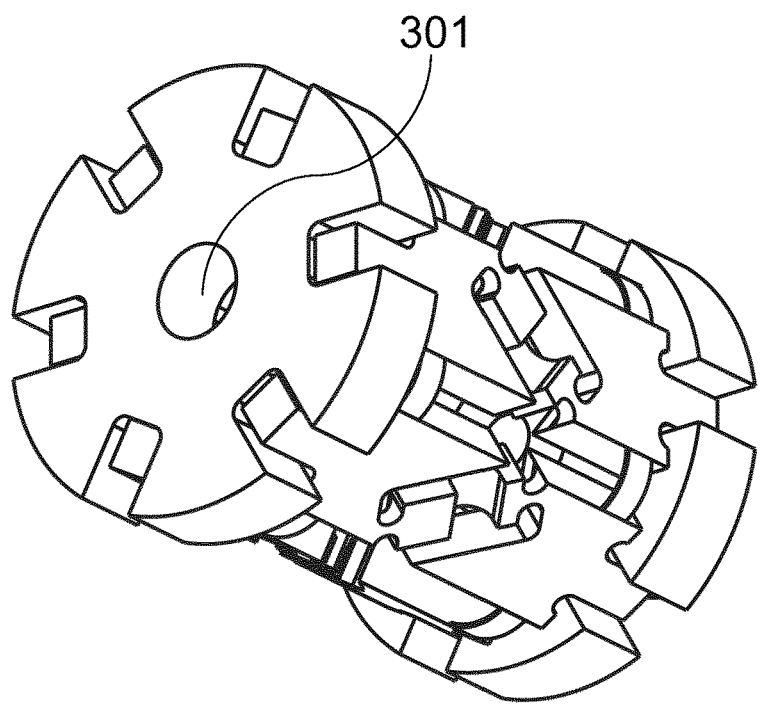

FIG. 8A shows a side view and FIG. 8B a perspective view of the rolled-up sensor structure, which is closed on both sides with a first lid 610 on the first contact structure 110 and a second lid 620 on the second contact structure 120.

The first and second lids 610, 620 include correspondingly formed grooves formed to receive the first pins 710 of the first contact structure 110 and/or the second pins 720 of the second contact structure 120. Since the first pin 710 and the second pin 720 can each be fixedly connected to the first lid 610 and the second lid 620 (for example by way of an adhesive connection, soldered connection, or welded connection), a high stability of the sensor arrangement can be achieved in this way. For example, the first lid 610 and the second lid 620 can be metal lids that form a rigid mechanical structure to receive the forces or torques to be measured by the sensor assembly.

In a central region along the axial axis of the cylinder-shaped or prism-shaped sensor arrangement, FIG. 8B also shows an opening 301 that can be formed on both sides and widens in an interior area to the aforementioned interior space 300. Through these openings 301 and interior space 300, other instruments or lines or control elements can be passed through the sensor assembly. This through hole 301 can be threaded to mount thereon the sensor in the flow of force. The leads run in a hollow threaded pin and can thus be guided coaxially into the interior 300 of the push rod. To introduce force to the sensor elements 130 in the diagonal struts, the pins 710, 720 formed on the top and bottom sides of each segment can be used which engage in the grooves of the upper or lower lid 610, 620. The exemplary strain gauges 230 can in turn be formed inside (or outside) the prism-shaped sensor arrangement.

All remaining elements can be formed in the same way as already described in the previously shown figures.

Figure 9:
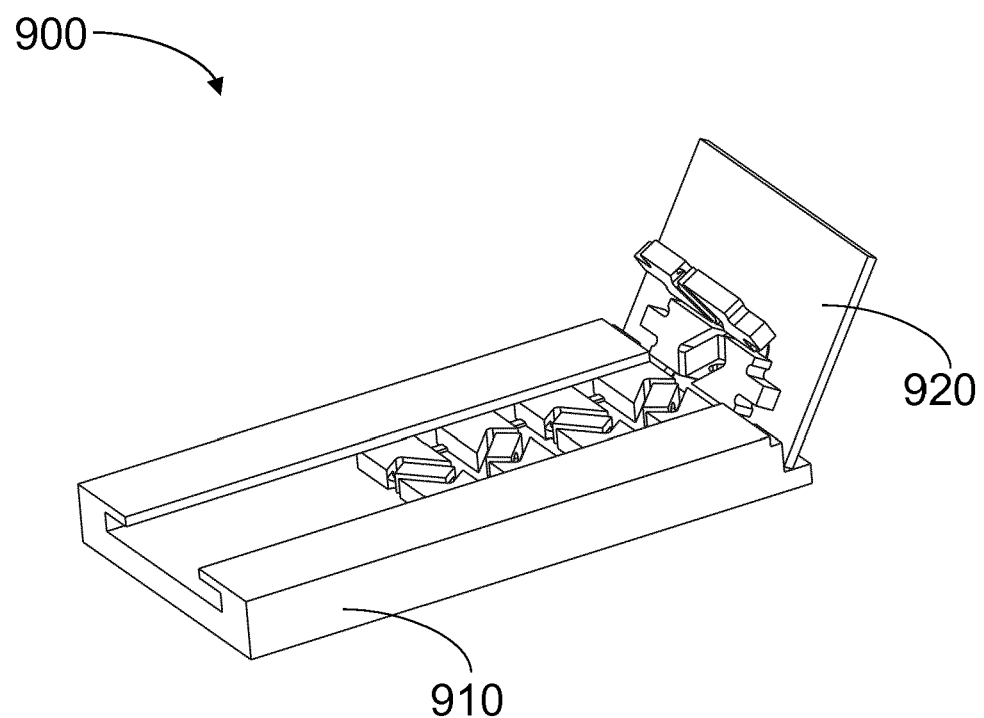
FIG. 9 shows a device for rolling up the sensor arrangement according to exemplary embodiments.

FIG. 9 shows a device 900 that can be used for rolling up the sensor arrangement. The device 900 includes a first section 910 (guide) and a second section 920 (angled section). In the first section 910 corresponding indentations/guides (e.g., as a T-slot) are formed, which allow the planar disposed sensor structure, as shown for example in FIG. 7, to be introduced and laterally displaced. The second portion 920 is tilted, for example at an angle of about 120° relative to the first portion 910.

This makes it possible that by means of pushing the planar sensor structure (see FIG. 7) through, the sensor sections 10, 20, . . . are each bent at an angle of approximately 120° relative to one another so that ultimately the rolled-up structure as seen in FIG. 6, 8A or 8B, for example, results. In this case, the second section 920 can in particular be flat (parallel to the first section 910) or tiltable about the angle. Alternately, the sensor structure then advances step by step and the second section 920 is tilted about the angle relative to the first section 910. The angle can be flexibly adjustable, for example.

Due to the planned position in certain applications (e.g., in a rotating push rod in a minimally invasive surgery), the lids 610, 620 must be aligned axially and parallel to each other, otherwise the existing eccentricity will result in unwanted movement of the end effector upon rotation of the exemplary push strut. For the purpose of aligning a preassembled module, it is possible to use a cylinder that is tailor-made as far as possible.

Figure 10:
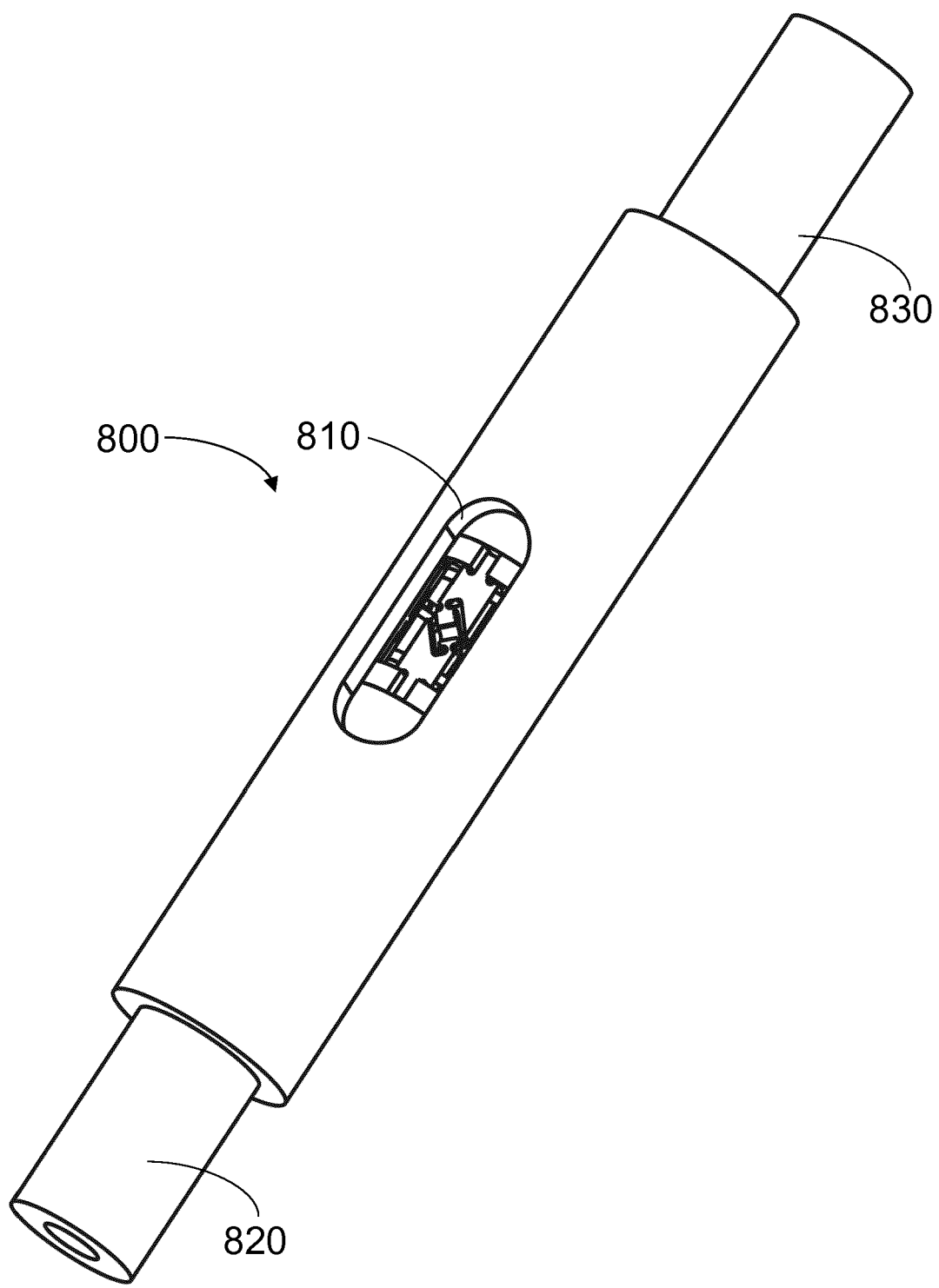
FIG. 10 shows an assembly aid for mounting to the sensor arrangement according to exemplary embodiments.

FIG. 10 shows an assembly aid 800 suitable for aligning the openings 301 in the first lid 610 and in the second lid 620 such that rotation of the first lid 610 about the axial axis causes rotation of the second lid 620 about an identical axial axis without lateral offset or eccentricity.

The rolled-up sensor structure as shown in FIG. 6 can be introduced there, wherein the lids 610, 620 can already be placed on the rolled-up sensor structure (see FIG. 8A, 8B). Optionally, however, the lids 610, 620 can also be subsequently inserted, i.e., the first lid 610 is inserted from one side of the mounting aid 800 and the second lid 620 is inserted from the other side. In order to ensure that the pins 710 of the first contact structure 110 move into the grooves of the first lid 610 and the pins 720 of the second contact structure 120 move into the corresponding grooves of the second lid 620, the window 810 shown (e.g., designed as a slot) can be used to rotate the sensor assembly accordingly.

By applying a force to the lids 610, 620, they are firmly pressed onto the rolled-up structure. For example, the force can be exerted using punches (or cylinders) 820, 830, which are inserted on both sides into the assembly aid 800 and which can produce a form fit between the components.

The components oriented in this way can then be joined together by gluing. For this process, the slot 810 can be used in the hollow cylinder through which the joints are accessible.

Because of the cylindrical arrangement, the assembly aid 800 ensures that the respective axial directions of rotation are aligned with each other and that the sensor assembly does not exhibit any imbalance or eccentricity when rotating (both lids rotate about the same axis of rotation).

After bonding, the sensor assembly can be removed from the assembly aid 800. A final joining step can include an end-face welding of the pins 710, 720 to the lids 610, 620. For example, micro-laser welding can be used for this purpose. To hide the weld, the length of the pins 710, 720 can be selected to be shorter than the thickness of the lids 610, 620.

The use of the pin design facilitates initial assembly of the assembly and provides for spatial (and thus thermal) separation between the heat-sensitive components seated on the inside and the weld.

Further advantages of exemplary embodiments can be summarized as follows:

Compared to the known sensors, the structure of the deformation body is changed, so that it can first be manufactured by planar processes. These planar processes include, for example, micro-machining on the front side and/or the back side and then an exemplary cutting process (e.g., laser cutting). The strain gauges 230 can subsequently be applied and connected to the resulting planar structure. It is particularly advantageous that the entire structure and the connection technology can be automated in planar manufacturing steps using established technologies (such as wire bonding). Finally, the force sensor (sensor arrangement) is formed by rolling up the deformation body equipped with strain gauges, whereby the final hexapod structure is formed.

In order to be able to carry out the advantageous planar fabrication, the passive ball joints of the hexapod of the known structures are replaced by flexure joints. For example, these flexure joints 111, 112, . . . can comprise a sufficiently ductile material that provides joint functionality. The variable-length struts (sensor elements 130), which are held by the flexure joints 111, 112, . . . , can be formed by the bridge structure shown. This bridge structure ensures that not only can the variable-length active degree of freedom be detected, but also that the resulting strain is increased (by way of the mentioned lever effect, see FIGS. 4 and 5). This allows an increased sensitivity of the sensor arrangement formed.

Further advantages of exemplary embodiments can be summarized as follows:

The planar production enables high-volume production at low cost. For example, the deformation body can be produced by means of micro-machining, galvano-molding, a micro-injection process or 3D-printing.

For the micro-machining, there are advantages in terms of the equipment needed for the machining, which according to exemplary embodiments only needs to be movable during in the manufacturing process in three axes instead of five axes, as is necessary in conventional sensor arrangements.

In addition, several milled parts can be produced on an exemplary steel sheet (batch process), which can also shorten the set-up time.

Furthermore, methods established for the construction technique and the connection technique, for example wire bonding for contacting the measuring elements or lithography for structuring the conductor tracks, can be used.

Likewise, miniaturization can be further advanced since the processing can be carried out batchwise and the deformation body can be handled as a composite.

The manufacturing steps are also automatable, so that the miniaturization is limited only by the precision of the machine used and the technology thereof.

The force sensor or the sensor arrangement is formed by a simple rolling up process such that there is a hole in the middle through which further elements for an exemplary surgical robot, such as a push rod or other feed-in devices used for opening and closing an end effector, can be fed.

Finally, the sensor optimally utilizes the given installation space (lateral surface of the cylindrical instruments), which is not the case with the known sensors for multi-axial measurements (as, for example, with a sun gear structure). According to embodiments, all webs are disposed in a plane or circular disk.

The features of the invention disclosed in the description, the claims and the figures can be essential for the realization of the invention either individually or in any combination. Although the invention has been illustrated and described in detail by way of preferred embodiments, the invention is not limited by the examples disclosed, and other variations can be derived from these by the person skilled in the art without leaving the scope of the invention. It is therefore clear that there is a plurality of possible variations. It is also clear that embodiments stated by way of example are only really examples that are not to be seen as limiting the scope, application possibilities or configuration of the invention in any way. In fact, the preceding description and the description of the figures enable the person skilled in the art to implement the exemplary embodiments in concrete manner, wherein, with the knowledge of the disclosed inventive concept, the person skilled in the art is able to undertake various changes, for example, with regard to the functioning or arrangement of individual elements stated in an exemplary embodiment without leaving the scope of the invention, which is defined by the claims and their legal equivalents, such as further explanations in the description.

LIST OF REFERENCE SYMBOLS 10, 20, . . . 60 Sensor sections
101 Ground

110 First contact structure
111, 121 Joints
115 Connecting point
120 Second contact structure
130, 131, . . . Sensor elements
210 First connecting sections
211, . . . 216, 221, . . . 226 Contact pads
219 First comb structure
220 Second connecting sections
229 Second comb structure
230, 231, . . . Strain gages/Strain gauge strips
300 Interior space
301 Lid openings
330 Additional sensor element (s)
331 Recess
332 Thinned section of a bridge structure/connecting section
610, 620 Lid
710, 720 Pins
800 Mounting aid
810 Window
820,830 Punch/cylinder
900 Roll-up device
910 Guide for planar sensor structure
920 Unwound section of the rolling device

The invention claimed is:

1. A sensor arrangement for measuring at least one component of a force or a torque, the sensor arrangement comprising:
a first contact structure and a second contact structure between which the at least one component of the force or torque is to be measured; and
a plurality of sensor elements, each of the plurality of sensor elements is connected by way of a respective first joint to the first contact structure and by way of a respective second joint to the second contact structure, and each of the plurality of sensor elements are configured to measure the component of the force or the torque between the first contact structure and the second contact structure,
wherein the first contact structure, the second contact structure, and the plurality of sensor elements form a rolled-up sensor structure that extends in a jacket-like or spiral-like manner along a surface of the sensor arrangement, and
wherein a circumference of the rolled-up sensor structure has an axial seam at which axial sides of the rolled-up sensor structure contact each other or at which there is a gap between the axial sides, wherein the gap is open or the gap is closed by adhesive or solder.

2. The sensor arrangement of claim 1, wherein the plurality of sensor elements comprise three sensor elements defining a tripod structure, or six sensor elements defining a hexagonal structure, the plurality of sensor elements being inclined relative to the first contact structure and the second contact structure in order to thereby independently measure three different force components and/or three different torque components.

3. The sensor arrangement of claim 1, wherein the plurality of sensor elements each comprise a bridge structure having a thinned portion and at least one strain gauge on the thinned portion to measure a strain on the thinned portion as a result of an application of the force or torque on the sensor arrangement.

4. The sensor arrangement of claim 3, wherein the bridge structure has a U-shaped cross-sectional profile with two opposite sections between which a recess is formed, the two opposite sections are bridged with a connecting section as a thinned section, and
the first contact structure and the second contact structure couple at the two opposite sections, and the strain gauge is formed on the connecting section such that the component of the force or the torque applies a lever force to the connecting section and leads to an increase in strain.

5. The sensor arrangement of claim 1, wherein the first joint and the second joint are both flexure joints having a reduced, square or round, cross-sectional area.

6. The sensor arrangement of claim 1, further comprising:
a first lid and a second lid, wherein the first lid is attached to the first contact structure and the second lid is attached to the second contact structure, and the first and second contact structure include means for force input or force output.

7. The sensor arrangement of claim 6, wherein
the sensor arrangement is useable for power transmission to a tool,
the first lid and the second lid define an axial axis about which the jacket-shaped sensor structure is disposed, and the first lid and the second lid each have an opening through which the axial axis passes, and
the rolled-up sensor structure defines an interior space for permitting routing through the sensor arrangement of optical and/or electrical leads and/or elements for operating the tool along the axial axis.

8. The sensor arrangement of claim 7, wherein
the first contact structure and the second contact structure each comprise a plurality of segments,
a sensor element is formed between two respective segments of the plurality of segments to form a plurality of sensor sections, each of the plurality of sensor segments comprising a pin extending away from the sensor module, and
the first lid and the second lid each have a plurality of grooves disposed such that the pins of the first and second contact structures are insertable into the grooves.

9. The sensor arrangement of claim 8, further comprising:
additional sensor elements on the segments of the first contact structure or on the segments of the second contact structure,
wherein, in each case, a sensor element is connected to one of the additional sensor elements to form a half-bridge circuit.

10. The sensor arrangement of claim 1, wherein
the first contact structure comprises a first comb structure and the second contact structure comprises a second comb structure for establishing a firm connection between the first contact structure and the second contact structure by way of an enlarged adhesion surface, and
the firm connection comprises at least one of the following connections an adhesive bond, a solder joint, and a welded joint.

11. A method for producing a sensor for measuring at least one force and one torque, the method comprising:
providing a planar sensor structure having a first contact structure and a second contact structure with a plurality of sensor elements connected in a joint-like manner therebetween; and
rolling up the planar sensor structure such that the first contact structure and the second contact structure and the plurality of sensor elements extend in the form of a jacket around an axial axis.

12. The method of claim 11, wherein the provision of the planar sensor structure comprises:
provide a flexible body;
structuring the flexible body to form the first contact structure and the second contact structure interconnected by bridge elements; and
forming at least one respective strain gauge on the bridge elements.

13. The method of claim 11, wherein rolling up the planar sensor structure further comprises:
inserting the planar sensor structure into a rolling device comprising a guide and an angled section, the guide being adapted to receive the planar sensor structure; and
moving the planar sensor structure toward the angled section so that the planar sensor structure is bent in sections to produce the jacket-shaped structure.

14. The method of claim 11, further comprising:
placing a first lid and a second lid on opposite sides of the rolled-up sensor structure;
inserting the rolled-up sensor structure in a cylinder or prism-shaped mounting aid; and
applying a pressure to the first and second lids to align the jacket-shaped sensor structure with axial symmetry.

* * * * *